United States Patent
Matschke

[11] Patent Number: 6,022,511
[45] Date of Patent: Feb. 8, 2000

[54] APPARATUS AND METHOD FOR GERMICIDALLY CLEANING AIR IN A DUCT SYSTEM

[75] Inventor: Arthur L. Matschke, Brookfield Center, Conn.

[73] Assignee: MolecuCare, Inc., Southport, Conn.

[21] Appl. No.: 09/112,500

[22] Filed: Jul. 9, 1998

[51] Int. Cl.[7] ........................................................ A61L 9/20
[52] U.S. Cl. .............................. 422/121; 422/24; 250/436
[58] Field of Search ................ 422/121, 24; 250/455.11, 250/436

[56] References Cited

U.S. PATENT DOCUMENTS

| | | |
|---|---|---|
| 3,798,879 | 3/1974 | Schmidt-Burbach et al. . |
| 4,201,916 | 5/1980 | Ellner . |
| 4,786,812 | 11/1988 | Humphreys . |
| 4,877,964 | 10/1989 | Taneka et al. . |
| 5,107,687 | 4/1992 | Candeloro . |
| 5,200,156 | 4/1993 | Wedekamp . |
| 5,219,534 | 6/1993 | Reynolds . |
| 5,330,722 | 7/1994 | Pick et al. . |
| 5,497,573 | 3/1996 | Stadjuhar et al. . |
| 5,523,057 | 6/1996 | Mazzilli . |
| 5,612,001 | 3/1997 | Matschke . |
| 5,635,133 | 6/1997 | Glazman . |

*Primary Examiner*—Elizabeth McKane
*Attorney, Agent, or Firm*—Bazerman & Drangel, PC

[57] ABSTRACT

A germicidal UV chamber for use on air passing through a duct system, such as a central air system which replace one or more sections of the duct and, in essence, becomes part of the duct work. Each chamber is in the form of one or more ellipsoid sections which focus the energy uniformly throughout the chamber. A chamber is mounted at each return vent to cleanse the air from a room as it returns to the duct system. In addition, where exterior contamination is feared, outside air entering the system may also be treated. Chambers may be connected by their respective ducts in series or in parallel.

20 Claims, 8 Drawing Sheets

APPARATUS AND METHOD FOR GERMICIDALLY CLEANING AIR IN A DUCT SYSTEM

BACKGROUND OF THE INVENTION

Airborne bacteria or other microorganisms permeate the air we breath. Some of these microorganisms with which we share our environment cause disease. Medical environments, such as hospitals, have a high degree of pathogens in the air and highly susceptible, weakened patients. The existence of biological weapons of mass destruction require protection of command centers, barracks, ships, and other closed environments against biological agents. Today's modern sealed high-rise structures with central air conditioning and heating, through duct systems, need protection from the spread of disease among its occupants and from colonies of microorganisms which may live in the duct system. Today, biologic protection is necessary on the battlefield and in the workplace, the hospital and the home.

Much effort has gone into trying to destroy atmospheric pathogens with only limited success. It has long been recognized that pathogens can be destroyed in the air if they are irradiated with ultraviolet (UV) light at a wavelength of 253.7 nanometers (Germicidal Wavelength). In order for the UV light to kill microorganisms, the UV rays must directly strike the microorganisms for a sufficient time. Because of the absolute necessity for antiseptic surroundings, UV lamps of the required Germicidal Wavelength are often used in operating rooms, wards, and nurseries of hospitals.

The exposure to UV light necessary to kill microorganisms is a product of time and intensity. However, due to the dangers to humans of irradiation from wide-spread use of UV lamps, exposure to UV light has been limited by government regulations. The current occupant exposure limit (ACGIH, NIOSH standard) for 254 m ultraviolet germicidal wavelength ceiling fixtures is 6000 $\mu$watts seconds/cm$^2$ in one eight hour day. Thus, the maximum allowed intensity per second is 0.2 $\mu$W/cm$^2$. At this intensity, eight hours at the allowed exposure level is required to gain a 90% kill of *Mycobacterium tuberculosis* (90% kill-value =6200$\mu$watts/cm$^2$) at head height. For 100% kill using the same standard, the value is 10,000 $\mu$watts/cm$^2$, requiring 13.89 hours of exposure. The required low intensity, and resulting long exposure times, permit migration of microorganisms out of range of the UV lamp and result in accumulation of microorganisms which survive the UV lamp in the room. Increasing air circulation does not increase exposure of microorganisms. It only moves organisms past the UV lamp without sufficient exposure.

To overcome these problems there have been various attempts to circulate air passed UV sources in enclosures which acts to shield the UV irradiation from the room's occupant. Usually, such systems are free-standing, or wall or ceiling mounted devices which circulate the air in a single room through the enclosure and, accordingly, whose protection is confined to that room. See, for example, U.S. Pat. No. 5,330,722 to Pick, which discloses a germicidal air purifier which draws air through a chamber in which there is mounted an ultraviolet source which acts to kill microorganisms caught in the filter structure. Similarly, U.S. Pat. No. 5,612,001 to Arthur L. Matschke, discloses a germicidal air cleansing enclosure having an internal ellipsoid chamber which contains UV lamps along the major axis of the ellipsoid. The unit is free-standing and treats air in a single room.

While a system such as that disclosed in U.S. Pat. No. 5,612,001 to Arthur L. Matschke, may be highly effective to cleans the contents of a single room, normal air conditioning and heating ducts would continue to allow circulation of untreated air into and out of a room. This allows untreated air containing pathogens from another room, or in the duct system, to enter the room and come into contact with humans before being treated and allow a certain amount of pathogens in a room to enter the duct system prior to being treated by the free-standing unit.

Various attempts have been made to place ultraviolet light sources in duct systems to germicidally cleans fluids such as air as they pass through the duct system. See, for example, U.S. Pat. No. 5,635,133 to Glazman, U.S. Pat. No. 5,200,156 to Wedekamp and U.S. Pat. No. 5,107,687 to Candelero. Each of these patents disclose an ultraviolet irradiation source in a duct to cleanse a fluid traveling through a duct of uniform diameter. The UV source is at right angles to the duct walls and UV energy is directed at least in part along the path of fluid flow. Thus, the level of ultraviolet energy varies along the flow path. As a result, the air circulated past the UV lamps in the prior art receive an uneven distribution of ultraviolet energy and a rapid diminution of energy levels outside the immediate area of the UV source. There has, however, been no attempt to use in the duct system an irradiation chamber which uniformly distributes UV light over an extended distance along the flow path of the fluid to uniformly irradiate all fluids traveling through the duct.

SUMMARY OF THE PRESENT INVENTION

The present invention is a germicidal chamber which uniformly irradiates of all of the air passing through a duct system, such as a central air system. The chamber replace one or more sections of the duct and, in essence, becomes part of the duct work.

Each chamber is in the form of one or more ellipsoid sections which focus the energy uniformly throughout the chamber. A sphere is a form of ellipsoid and can be used in carrying forward the present operation. The chamber is connected to the duct so that all air drawn into the duct system must pass through the chamber. To accomplish this, each chamber is integral with the duct forcing all of the air in the duct on the upstream side to pass through the chamber. Such a system allows a chamber to be mounted at each return vent to cleanse the air from a room as it returns to the duct system. In addition, where exterior contamination is feared, such as in a germ warfare situation, outside air entering the system may also be treated.

Chambers may be connected by their respective ducts in series or in parallel. A single chamber may be formed from a series of ellipsoids in order to allow intense uniform irradiation over an extended distance in relatively narrow duct-work, thereby substantially increasing the exposure per unit of power consumption.

DESCRIPTION OF THE PREFERRED EMBODIMENT

Figure 1:
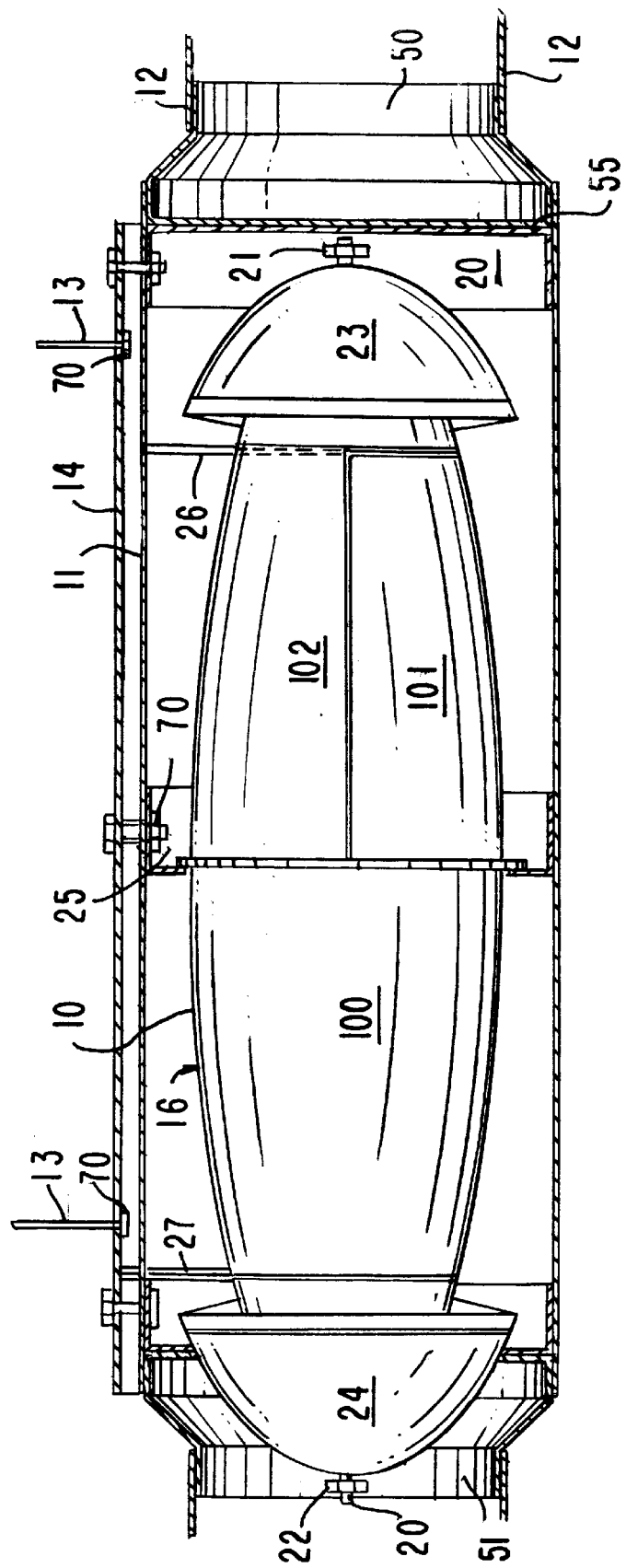
FIG. 1 is a partial cut-away front view of a chamber, in accordance with the present invention, with the shell wall removed.
Figure 2:
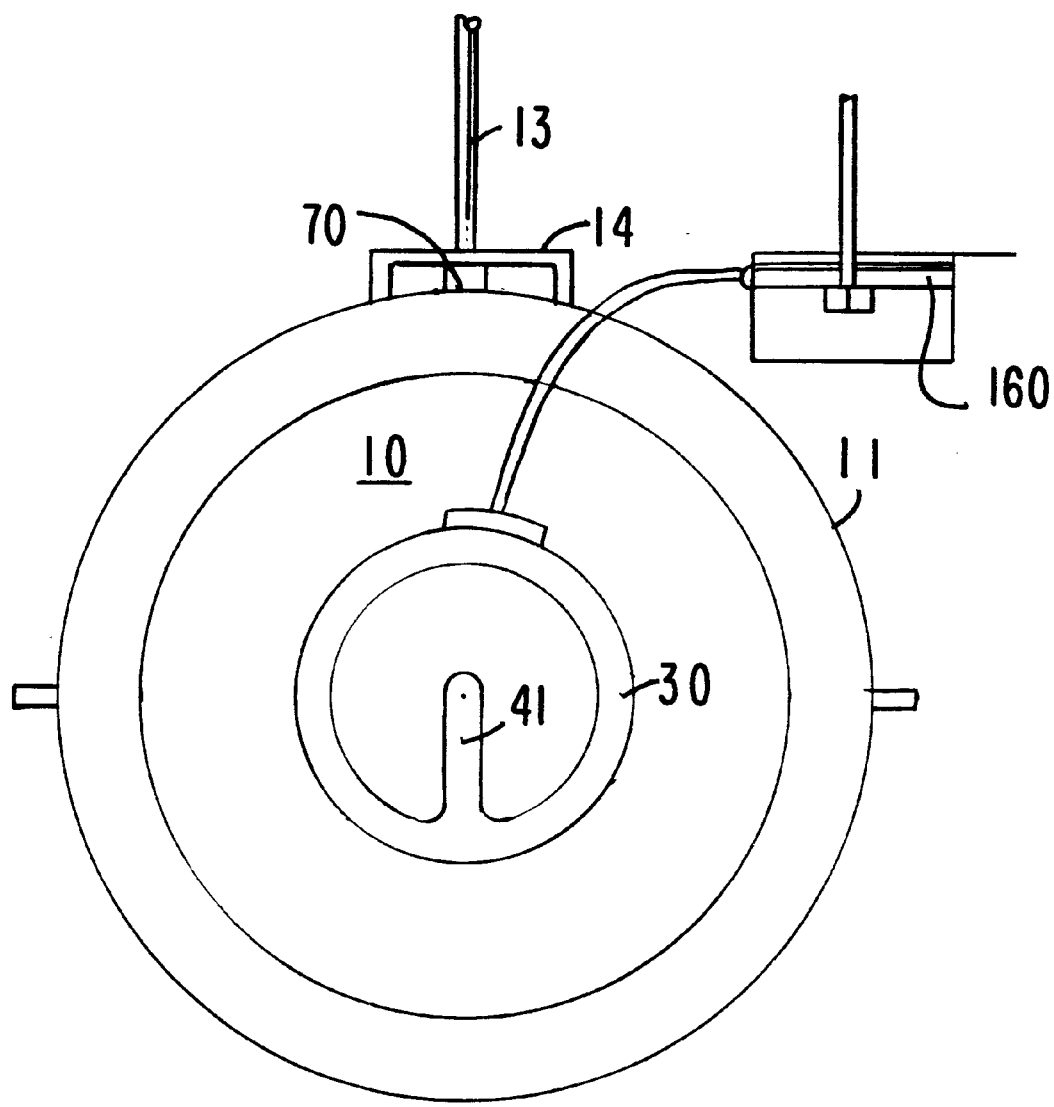
FIG. 2 is a cross-sectional view of FIG. 1.

In the present invention, the duct work of a central air system is modified to replace a portion of the duct with an ellipsoidal UV chamber 10 which becomes part of the central air duct system. Air is normally circulated through the central air system including through the chamber 10 by the HVAC fan.

The germicidal cleansing chamber 10 is mounted within a shell 11 connected to an air duct 12. The shell 11 can be used to insulate the chamber from extremes of temperature and provide alternatives for finishes to give the chamber 10 an appearance that will allow it to be hung under the ceiling. The shell 11 has mounted on it mounting spine 14. The spine 14 is of sufficient crosssection and strength to carry the chamber 10 and may be U-shaped to allow positioning and proper mounting of the shell 11. The spine 14, and thus shell 11 and germicidal cleansing chamber 10, are mounted to the ceiling by conventional mounting means such as suspension rods, cables or straps 13. Each of the suspension means 13 are attached to mounting spine 14 by conventional means such as nut 70.

Figure 3:
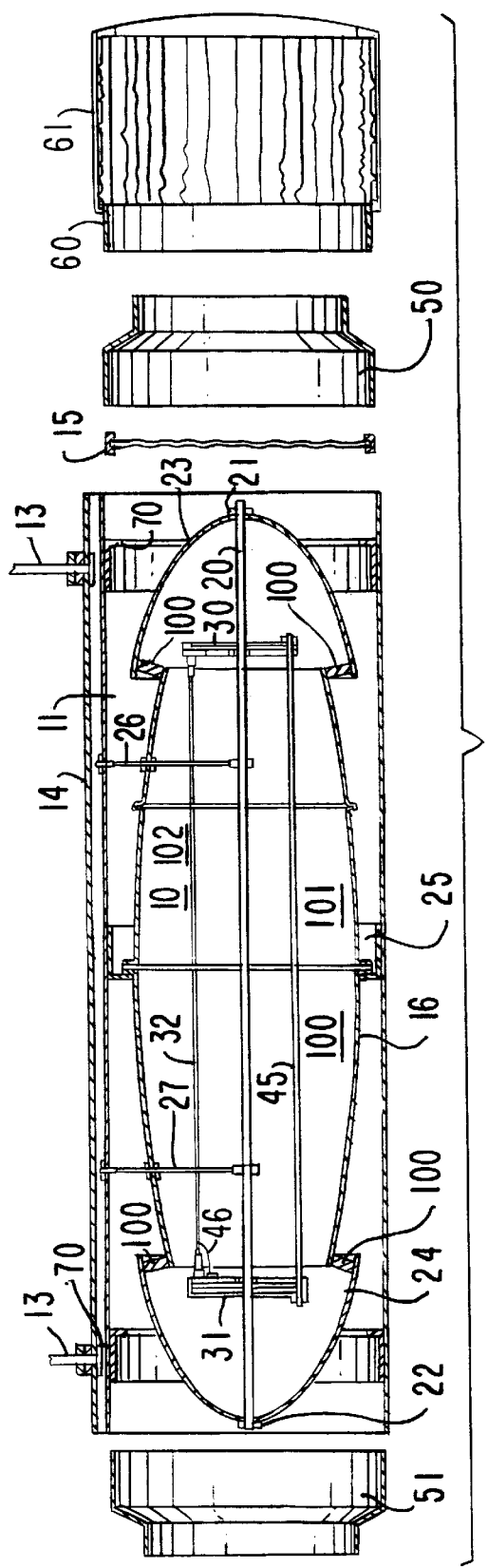
FIG. 3 is an partially exploded cross-sectional view of the chamber.

As seen most clearly in FIG. 3, central rod 20 is used to hold chamber 10 in compression. Rod 20 is threaded at either end with end nuts 21 and 22 mounted thereon. These end nuts 21 and 22 act to retain the chamber 10 and the elements positioned around the central threaded rod 20 under moderate compressive force. At either end of the elliptical central portion 16 of chamber 10 are end caps 23 and 24 positioned around rod 20 in contact with nuts 21 and 22, respectively. The end caps 23 and 24 are spaced from central portion 16 by spacers 100. The central portion 16 of chamber 10 may be composed of a number of sections 101, 102, and 103 to allow access into the interior of chamber 10. The central portion 16 and the end caps 23 and 24 may be made from spun aluminum or be formed from a molded material having aluminum or other highly UV reflective material deposited on the interior.

The central portion 16 of chamber 10 is an ellipsoid. The end caps 23 and 24 are displaced paraboloids which share loci with the elliptical chamber. Normally, when mounted in a duct, it will be in the form of an elongated chamber as seen in FIGS. 1 and 3. However, the ellipsoid may be a sphere.

The chamber 10 is attached to a bulkhead 25 mounted in shell 11. Flexible attaching means such as a wires or straps 26 and 27 are mounted on shell 11 and pass through grommeted holes in the central portion 16 of the elliptical chamber 10 such that the openings (not shown) are sealed. Wires or straps 26 and 27 loop around the rod 20 but are not in contact with rod 20 except when nuts 21 and 22 are removed for maintenance. During maintenance the wires or straps come in contact with rod 20 to support the chamber 10.

The bulkhead 25 is in sealed engagement with both the shell 11 and the central portion 16 of chamber 10 at the mid-point of central position 16. As air is drawn into the duct system, it will be pass through chamber 10, entering in the space between the end cap 23 and central portion 16. Since the chamber 10 can be mounted in existing duct systems, the air will be drawn into the chamber 10 by the circulation system of the duct system, such as a building HVAC fan.

Figure 4:
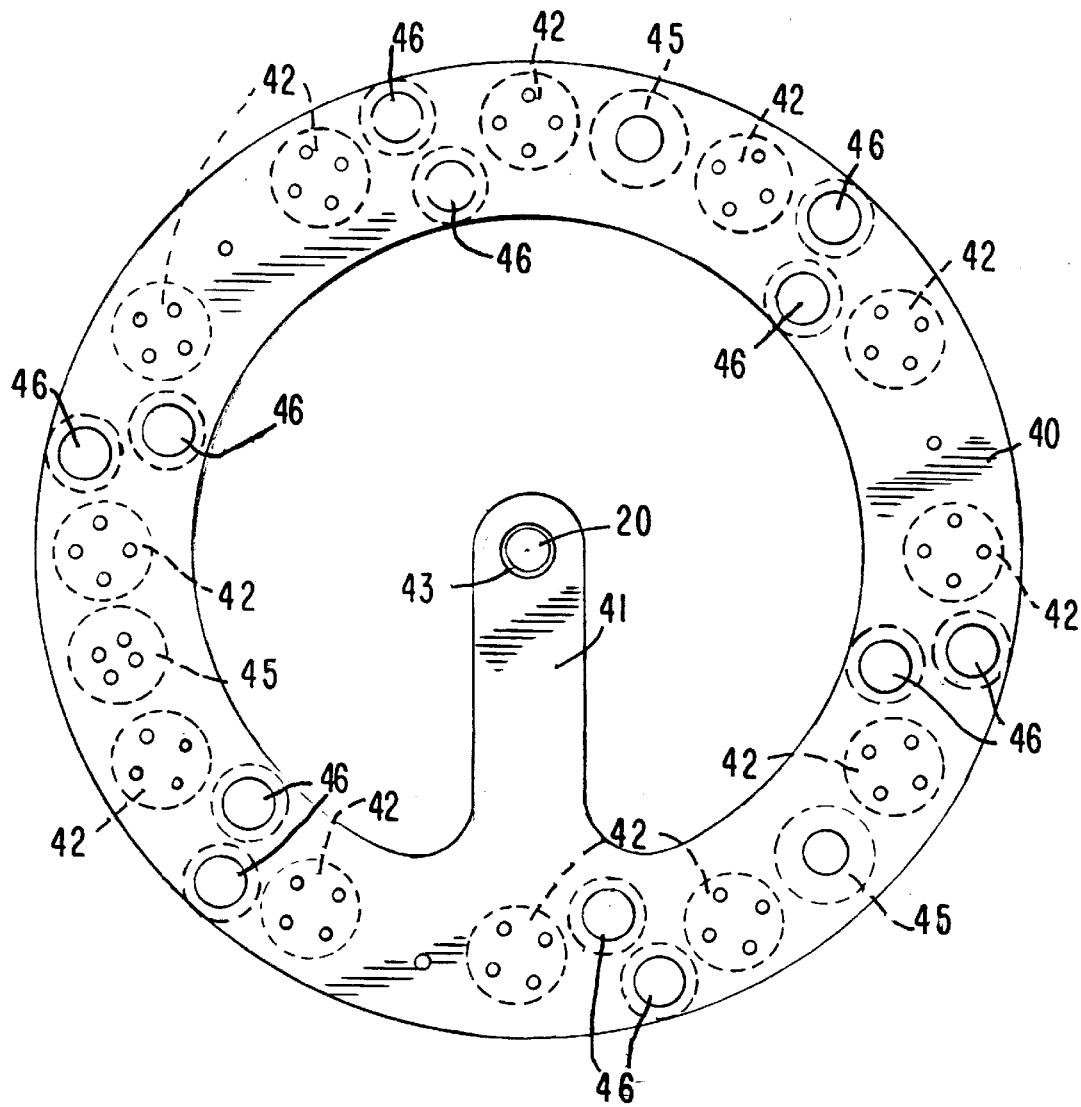
FIG. 4 is a front view of a mounting and sensor ring which is positioned in the chamber.

Mounted in the chamber 10 around rod 20 are mounting rings 30 and 31 between which UV light sources 32 are positioned. As seen in FIG. 4, mounting rings 30 and 31 are flat annular rings with a central bearing arm 41. Also attached to the mounting rings 30 and 31 are positioning rods 45 which hold the mounting rings 30 and 31 in their respective positions along rod 20 position to allow mounting of UV sources 32. The mounting rings 30 and 31 have socket means 42 for receiving and electrically connecting the UV light sources 32 to its ballast 160. The number of UV light sources will be determined by the overall requirements of the system. The central bearing arm 41 of mounting rigs 30 and 31 extends past the principle axis of the ellipsoid chamber with an arbor bearing 43 on that axis. Rod 20 passes through the arbor bearing 43. Mounting rings 30 and 31, with the UV source 32 and positioning rods 45 can freely rotate around rod 20. The mounting rings 30 and 31 include an interior circuit board (not shown) protected by the structure of the mounting rings 30 and 31 from UV irradiation.

Also mounted on mounting rings 30 and 31 are conventional UV sensors 46 to determine if each of the UV sources is generating UV light at acceptable levels. Such sensors 46 can, for example, consist of a fiber optic bundle positioned against the UV light source 32 and a conventional UV photo diode sensor (not shown). The diode signal may, in turn, be connect to a communications means to inform the user if one or more of the lamp's intensity has fallen off sufficiently to require replacement.

This method of mounting the lamp array improves accessibility to the lamps, reduces vibration and shock loads on the lamp sensors 46 and electrically isolates the UV source 32. The nuts 21 and 22 at either end of rod 20 hold the various elements of the chamber 10 in compression, thereby, assure a mating seal between section 101, 102 and 103 of central section 104 while adding rigidity to the chamber 10 as a whole. Rod 20 may be further supported by guide wire hangers located between the caps (not shown).

The chamber may be simply located in an existing duct system at a return vent or elsewhere. Adapters 50 and 51 on either side of shell 11 mate the chamber to a duct system preferably at or near a return air register. A pre-filter 55 may be mounted on the upstream side between the adapter 50 and shell 11 for the removal of debris. If the duct system is below a dropped ceiling, drum 60 may contain the pre-filter 61 and becomes the intake for the chamber.

Because of the elliptical configuration of the body portion in conjunction with the effect of the parabolic end caps, the UV light generated by the UV light source is evenly dispersed throughout the extended length of the chamber 10. Any point in the chamber 10 receives the same quantity of UV light in all directions as any other point within the chamber 10. The formation of the walls of the chamber 10 by spinning and the qualities of aluminum from which it is spun, acts to ensure the greatest part of the energy generated by the UV light sources 32 is reflected back into the chamber 10 rather than being absorbed by the walls of the chamber. The effect of UV irradiation on a microorganism is dependent on both UV intensity and length of time of exposure to the UV irradiation. Since the walls are highly reflective, the irradiation intensity created reaches a steady state which is substantially greater than the output of the lamps and, because of the configuration, is evenly distributed through the chamber.

Figure 8:
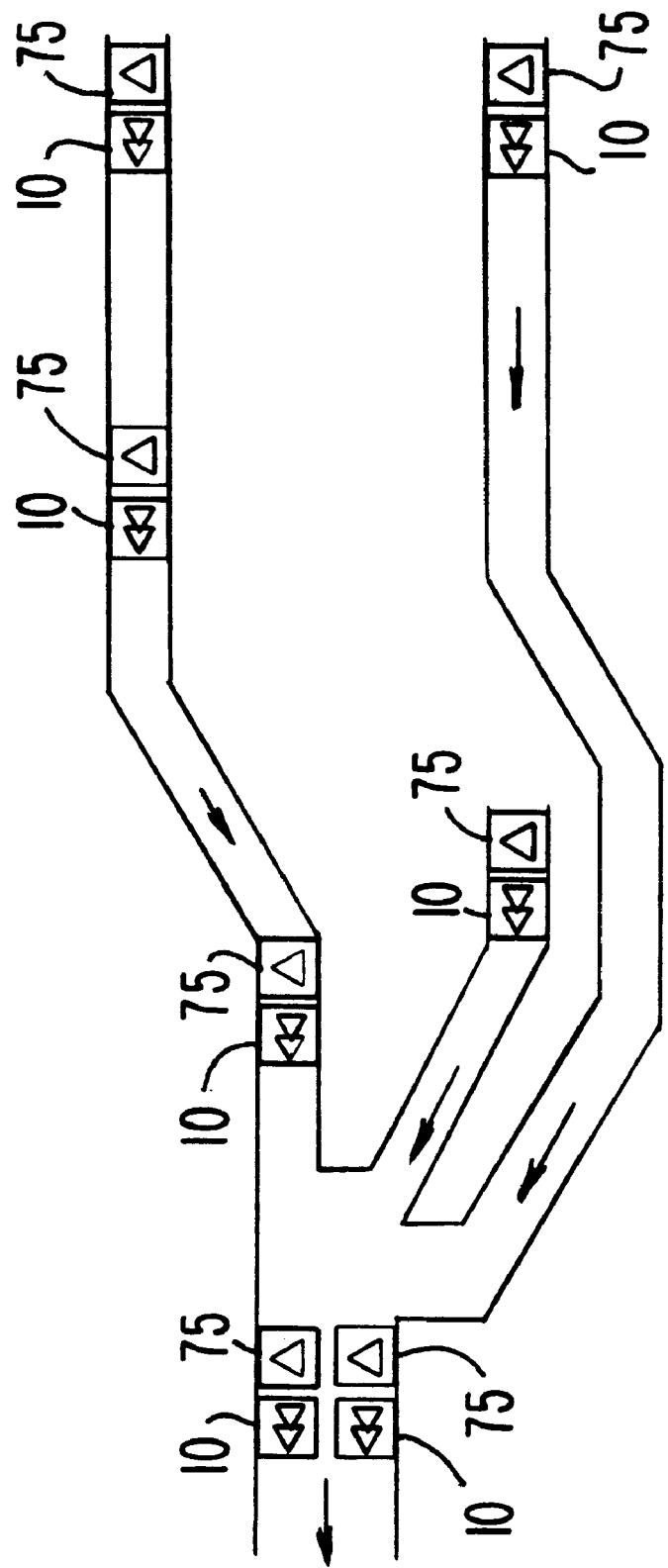
FIG. 8 is a schematic diagram showing placement of the chambers in the duct system.

In most cases, the chamber 10 should be mounted in association with the return air vent to allow the air to be cleansed of the room occupants' microorganism. As seen in FIG. 8, chambers 10 in combination with returns 75 may be mounted in series or in parallel. To handle large air volume flows such as return air from several rooms, a number of units can be placed in parallel, that is sideby-side, so the volume is divided between the units for cleansing as seen in FIG. 8. Where germ warfare or other contaminants may enter the building through outside sources, one or more chambers 10 should also be mounted on the intake to the air conditioning, heating or other circulation system to assure that air from any source is decontaminated.

Normally, duct systems are designed such that air is intended to flow in one direction. As noted above, the system of the present invention is normally located at the return air duct side of the system and air is drawn through the chamber 10 in one direction. Air flow through the chamber 10 is, in actuality, reversible with the same germicidal performance regardless of direction of air flow. On occasion, such reverse air flow occurs due to accidental or natural pressure changes that occur through occurrences such as elevator door operation or outdoor temperature change. Any such reversal will not affect the germicidal effect of the present machine. It is preferable that the germicidal system of the present invention be in continuous operation to compensate for air flow directional changes, such as when the central system fan is not creating enough pressure to overcome atmospheric or other building air flow differentials.

Figure 5:
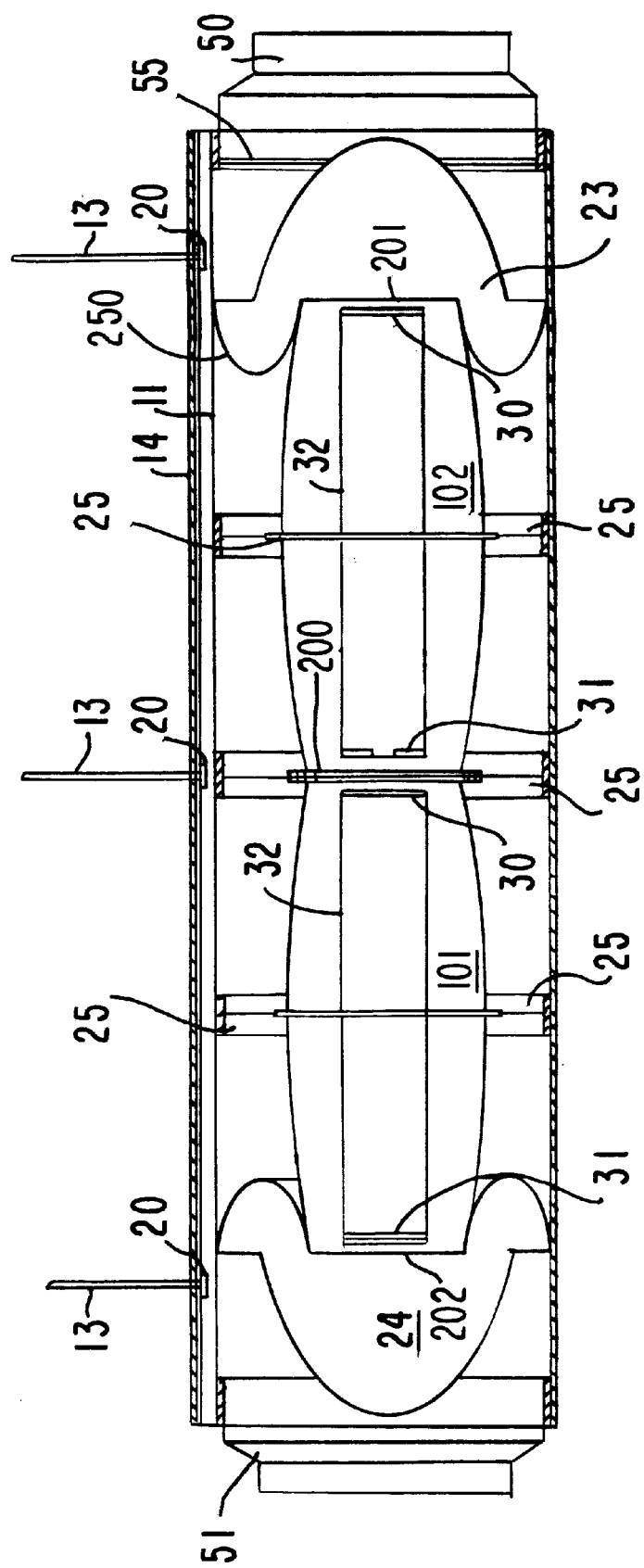
FIG. 5 is a cross-sectional view of an alternate embodiment of the present invention where the chamber is formed from two or more ellipsoids.
Figure 6:
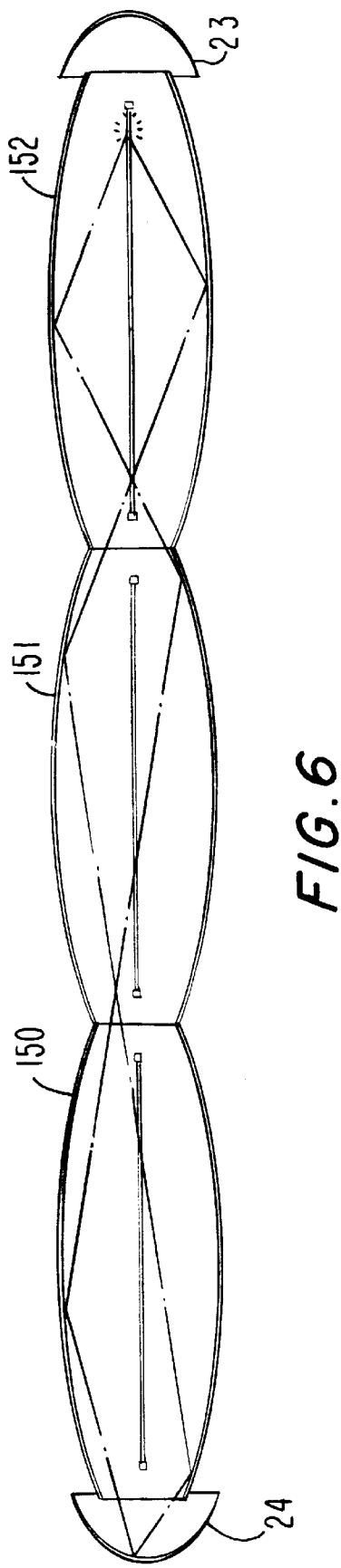
FIG. 6 is a schematic diagram showing the path of light along a multi-ellipsoid chamber.
Figure 7:
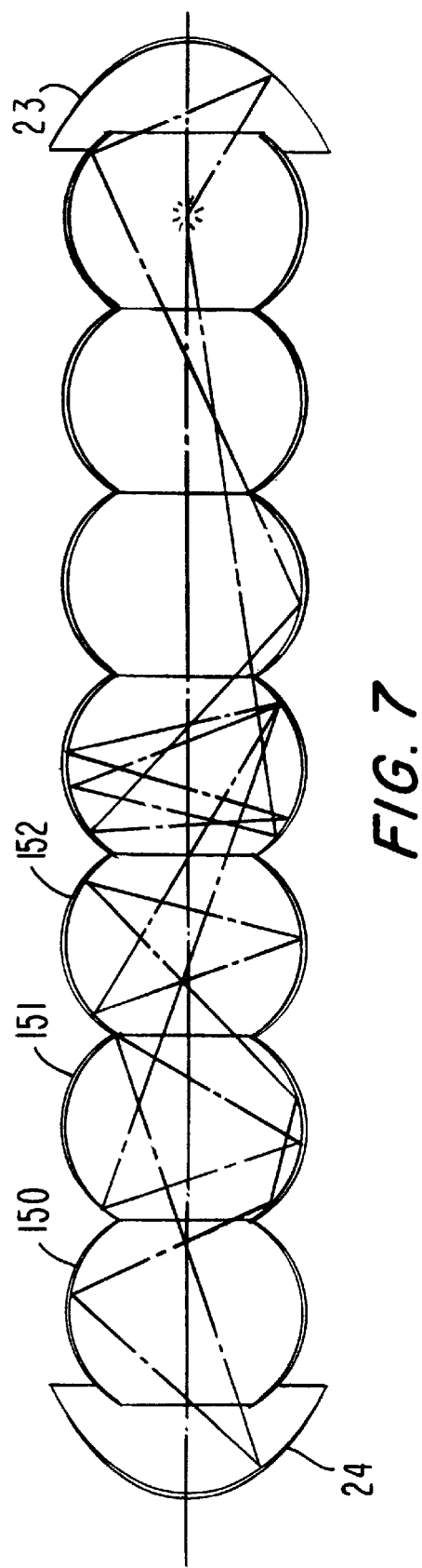
FIG. 7 is a schematic diagram showing the path of light along a multi-ellipsoid chamber where the ellipsoid chamber is formed from spheres.

FIGS. 5, 6 and 7 show a further embodiment of the invention. Given that the irradiation is evenly distributed throughout the chamber, the percentage of microorganisms destroyed would be dependent on the intensity of the irradiation and the residence time for an individual microorganism to pass through the chamber. Thus, extending the length of the chamber increases exposure at a given UV irradiation level. On the other hand, duct works are relatively narrow and places physical limits on the width of a chamber 10. In the embodiment of FIGS. 5, 6 and 7 two or more truncated elliptical sections are combined to extend the exposure time of a microorganism at a constant irradiation level, as more fully discussed below.

The chamber 10 is formed from truncated elliptical sections 101 and 102 which are symmetrical and mate at corresponding points along their axis. A greater number of sections may be used and each ellipsoidal section may be formed from one or more sub-sections. Where sections 101 and 102 meet, they form an intersection opening sufficient 200 to allow both the fluid and UV irradiation to pass between the sections, the first such section having an inlet opening 201 to allow the fluid to enter the chamber and the last such ellipsoidal element having an exit opening 202 to allow the fluid to exit the chamber. It is contemplated that the sections 101 and 102 will intersect in a plane at right angle to the principle axis of the sections 101 and 102. If so, the intersection opening will be in the form of a circle. The radius of the intersection opening should be equal to or less than 0.16 times the distance of the total chamber ellipsoid length (l) plus the diameter of the ellipsoid section at its widest point (d), i.e., Radius $\leq 0.16$ (l+d), to gain full advantage of the present invention. However the plane of intersection of the intersection may not be at right angles to the principal axis of sections 101 and 102. In such cases, the sections 101 and 102 could meet at an angle, allowing chamber 10 to be positioned around objects and/or to conform to the available space. The resulting intersection would be an ellipse or an ovate.

As can be seen in FIG. 6, a ray of light from any particular point along the energy sources in a chamber having multiple ellipsoid elements 150–152 will be evenly reflected throughout the chamber. Thus a single chamber of 12 foot length L with six ten watt lamps and two such 12 foot chambers interconnected as taught in the present invention with three ten watt lamps in each chamber will have the same UV energy level throughout at steady state but the tandem chamber will be twice as long, take twice as long for the microorganism to traverse and thus receive twice the exposure to the irradiation, i.e., (irradiation intensity×time), with the same energy input. Conversely, if you put six 10 watt lamps in each elliptical element of the chamber 10, the energy level and the exposure time will both double, increasing the microorganisms exposure four fold for twice the energy input. The present invention includes the use of spheres which are a form of ellipsoid, which, as seen in FIG. 7 will also function in the same manner to ensure even dispersion of UV energy throughout the chamber.

Each chamber has its own mounting rings 30 and 31 and is, in fact, similar in construction to the purely ellipsoidal chamber of FIGS. 1 and 3. A pre-filter 55 may be used.

While FIGS. 1 and 3 disclose the use of a sealed bulkhead 25 within the shell to ensure that all air passing through the ducts will pass through the chamber, the end caps 23 and 24 may have a rim 250 in engagement with the shell 14 as can be seen in FIG. 5. In this embodiment the rim 250 replaces the bulkhead 25 in sealing the air from flowing past the chamber 10 and channels the air into chamber 10. This eliminates the need for shell 11 on the central portion of the device. While FIG. 5 shows the use of a shell 11, in this intermediate area between the end caps, the shell can be removed and one or more ellipsoidal chamber sections 101 and 102 to be suspended directly by additional straps or rods 13 (not shown).

While the invention has been described as having a preferred design, it is understood that it is capable of further modification, uses and/or adaptations of the invention following in general principle of the invention and including such departures from the present disclosure as come within known or customary practice in the art to which the invention pertains, as may be applied to the central figures hereinabove set forth and fall within the scope of the invention of the limits of the appended claims.

I claim:

1. An apparatus for germicidally cleansing of a fluid comprising:

a chamber formed from a series of more than one interconnected truncated mating ellipsoidal sections each such section having openings at opposite ends along the section's longitudinal axis intercepting sections mating at such openings and forming intersection openings sufficient to allow both the fluid and to pass between the sections, the first such ellipsoidal section in the series forming the chamber having an inlet opening to allow the fluid to enter the chamber and the last such ellipsoidal section having an exit opening to allow the fluid to exit the chamber;

the inner wall of the chamber being made from an ultraviolet reflective material;

ultraviolet light sources positioned in one or more of said sections of the chamber;

the wall of each section being curved to direct the UV irradiation from the UV source throughout the entire chamber such that the energy in the UV chamber is uniform throughout the chamber and accumulates over time to reach a steady state energy level greater than that emitted by the UV source.

2. An apparatus according to claim 1 wherein each intersection opening, the inlet opening, and the exit opening are of the same size and configuration.

3. An apparatus of claim 3, where each intersection opening is circular having a radius equal to or less than 0.16 of the sum of the untruncated ellipsoidal length and the ellipsoidal diameter of the section at its widest point.

4. An apparatus according to claim 1 where the ellipsoidal sections are formed from a molded material on which a UV reflective material has been deposited.

5. An apparatus according to claim 1 wherein each ellipsoidal section is formed from spun aluminum.

6. An apparatus according to claim 1 where each ellipsoidal section is a truncated sphere.

7. An apparatus according to claim 1 where UV reflective end caps are positioned at the inlet opening of the first ellipsoidal section and the exit opening of the last ellipsoidal section to reflect UV irradiation back into the chamber.

8. An apparatus according to claim 1 where the interconnected truncated mating ellipsoidal sections are aligned along the same axis.

9. An apparatus according to claim 1 where the interconnected truncated mating ellipsoidal sections meet at an angle.

10. An apparatus for germicidally cleansing air in a duct system comprising:

a chamber formed from at least one truncated spherical section having an inlet opening to allow air to enter the chamber and a separate exit opening to allow air to exit the chamber;

ultraviolet light sources positioned in the chamber;

the internal walls of the chamber being made from an ultraviolet reflective material and the walls of the chamber shaped to direct ultraviolet light into and upon the walls of the chamber uniformly throughout the chamber and such that the energy in the chamber accumulates over time to reach a uniform steady state energy level greater than that emitted by the UV source; and an adapter to mate the chamber with the duct system.

11. An apparatus according to claim 10, wherein the chamber is formed of a molded material on which a UV reflective material has been deposited.

12. An apparatus according to claim 10 wherein the chamber is formed from spun aluminum.

13. An apparatus according to claim 10, where the chamber is formed from more than one truncated spherical section.

14. An apparatus according to claim 13, where the truncated spherical sections intersect to form a circular opening having a radius of equal to or less than 0.16 of the sum of the untruncated ellipsoidal length and the ellipsoidal diameter of the section at its widest point.

15. An apparatus according to claim 13 where there are more than two interconnected truncated spherical sections which are aligned along the same axis.

16. An apparatus according to claim 13 where there are more than two interconnected truncated spherical sections which meet at angels to each other.

17. An apparatus according to claim 10, where UV reflective end caps are positioned at the inlet opening and the exit opening of the chamber to reflect UV irradiation back into the chamber.

18. An apparatus for germicidally cleansing air in a duct system comprising:

a chamber having an inlet opening to allow air to enter the chamber and a separate exit opening to allow air to exit the chamber;

ultraviolet light sources positioned in the chamber;

the internal walls of the chamber being made from an ultraviolet reflective material and the walls of the chamber shaped to direct ultraviolet light into and upon the walls of the chamber uniformly throughout the chamber and such that the energy in the chamber accumulates over time to reach a uniform steady state energy level greater than that emitted by the UV source;

an adapter to mate the chamber with the duct system; and

UV reflective end caps positioned at the inlet opening and the exit opening of the chamber to reflect UV irradiation back into the chamber, wherein air is circulated past the end caps and into the chamber in a space between the end caps and the chamber and the end caps form a seal with the ducts so that all air passing through the ducts must pass through the chamber.

19. An apparatus according to claim 18, wherein the chamber and end caps are held in position by a central rod.

20. An apparatus for germicidally cleansing of a fluid comprising:

a chamber formed from a series of more than one interconnected ellipsoidal sections each such section having openings at opposite ends along the section's longitudinal axis, intercepting sections mating at such openings and forming intersection openings sufficient to allow both the fluid and UV irradiation to pass between the sections, the first such ellipsoidal section in the series forming the chamber having an inlet opening to allow the fluid to enter the chamber and the last such ellipsoidal section having an exit opening to allow the fluid to exit the chamber;

the inner wall of the chamber being made from an ultraviolet reflective material;

ultraviolet light sources positioned in one or more of said sections of the chamber;

the wall of each section being shaped to uniformly distribute the irradiation from the UV source throughout the entire chamber such that exposure of a microorganism passing through the chamber is extended without an increase in UV input power.

* * * * *